(12) United States Patent
Merkel et al.

(10) Patent No.: US 8,252,965 B2
(45) Date of Patent: Aug. 28, 2012

(54) METHOD FOR SEPARATING HALOCARBONS

(75) Inventors: Daniel C. Merkel, West Seneca, NY (US); Hsueh Sung Tung, Getzville, NY (US); Konstantin A. Pokrovski, Williamsville, NY (US)

(73) Assignee: Honeywell International Inc., Morristown, NJ (US)

( * ) Notice: Subject to any disclaimer, the term of this patent is extended or adjusted under 35 U.S.C. 154(b) by 336 days.

(21) Appl. No.: 12/540,252

(22) Filed: Aug. 12, 2009

(65) Prior Publication Data

US 2010/0048961 A1    Feb. 25, 2010

Related U.S. Application Data

(60) Provisional application No. 61/091,034, filed on Aug. 22, 2008.

(51) Int. Cl.
*C07C 21/00* (2006.01)

(52) U.S. Cl. ........ 570/216; 570/160; 570/164; 570/177; 570/178; 570/189

(58) Field of Classification Search .................. None
See application file for complete search history.

(56) References Cited

U.S. PATENT DOCUMENTS

| | | | |
|---|---|---|---|
| 3,557,226 A | 1/1971 | Sherk | |
| 3,755,475 A | 8/1973 | Fuhrmann et al. | |
| 5,200,431 A | 4/1993 | Dattani et al. ................. | 570/178 |
| 5,211,817 A * | 5/1993 | Adams et al. ................... | 203/82 |
| 5,456,841 A | 10/1995 | Lee ................ | 210/640 |
| 5,582,014 A | 12/1996 | Lyon et al. ..................... | 62/606 |
| 5,665,266 A | 9/1997 | Mahler et al. .................. | 252/67 |
| 5,858,066 A | 1/1999 | O'Brien et al. ................... | 95/48 |
| 5,874,659 A | 2/1999 | Lusson | |
| 5,986,151 A | 11/1999 | Van Der Puy ................. | 570/175 |
| 6,759,381 B1 * | 7/2004 | Johnson et al. ................. | 510/408 |
| 7,060,165 B2 | 6/2006 | Brandstater et al. ............ | 203/29 |
| 7,371,309 B2 | 5/2008 | Boehmer et al. ................. | 203/57 |
| 2007/0007488 A1 | 1/2007 | Singh et al. ..................... | 252/68 |
| 2007/0131535 A1 | 6/2007 | Shiflett et al. ................... | 203/50 |
| 2007/0197842 A1 * | 8/2007 | Mukhopadhyay et al. ... | 570/155 |

FOREIGN PATENT DOCUMENTS

| | | |
|---|---|---|
| EP | 0 472 391 | 2/1992 |
| EP | 537616 | 3/1995 |
| EP | 0878456 | 11/1998 |
| JP | 7280189 | 10/1995 |
| WO | WO9425419 | 11/1994 |
| WO | WO9630109 | 10/1996 |

OTHER PUBLICATIONS

U.S. Appl. No. 61/040,759, filed Mar. 31, 2008.

* cited by examiner

*Primary Examiner* — Sudhakar Katakam
(74) *Attorney, Agent, or Firm* — Bruce O. Bradford

(57) ABSTRACT

The invention provides a method for separating halocarbons. In particular, a method for separating 2-chloro-1,1,1,2-tetrafluoropropane (HCFC-244bb) from 2-chloro-3,3,3-trifluoropropene (HCFO-1233xf) based on differences in melting points of these compounds. More particularly the invention pertains to a method for separating HCFC-244bb from HCFO-1233xf which are useful as intermediates in the production of 2,3,3,3-tetrafluoropropene (HFO-1234yf).

20 Claims, No Drawings

METHOD FOR SEPARATING HALOCARBONS

CROSS REFERENCE TO RELATED APPLICATION

This application claims the benefit of U.S. provisional patent application Ser. No. 61/091,034 filed Aug. 22, 2008, which is incorporated herein by reference.

BACKGROUND OF THE INVENTION

1. Field of the Invention

The present invention provides a method for separating halocarbons. In particular, the invention provides a method for separating 2-chloro-1,1,1,2-tetrafluoropropane (HCFC-244bb) from 2-chloro-3,3,3-trifluoropropene (HCFO-1233xf) based on differences in freezing points of these compounds. More particularly the invention pertains to a method for separating HCFC-244bb from HCFO-1233xf, which are useful as intermediates in the production of 2,3,3,3-tetrafluoropropene (HFO-1234yf).

2. Description of the Related Art

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials associated therewith, it is desirable to use fluids having the lowest possible greenhouse warming potential in addition to zero ozone depletion potential. Thus there is considerable interest in developing environmentally friendlier materials for the applications mentioned above. Tetrafluoropropenes, having zero ozone depletion and low global warming potential, have been identified as potentially filling this need. However, the toxicity, boiling point, and other physical properties in this class of chemicals vary greatly from isomer to isomer. One tetrafluoropropene having valuable properties is 2,3,3,3-tetrafluoropropene (HFO-1234yf). Thus, there is a need for new manufacturing processes for the production of tetrafluoropropenes and in particular 2,3,3,3-tetrafluoropropene.

HCFC-244bb and HCFO-1233xf are intermediates in the production of 2,3,3,3-tetrafluoropropene (HFO-1234yf) which is well known in the art as described in U.S. Applications 20070007488 and 20070197842, the specifications of which are incorporated herein by reference. HFO-1234yf has been disclosed to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid.

Mixtures of two halocarbons are often inseparable using standard techniques, especially when then form a binary azeotrope or azeotrope-like composition. The prior art has suggested various methods of separating azeotropic mixtures of fluorocarbons. In this regard European patent application EP 0 472 391 suggests separating HFC-134a from a mixture containing hydrochlorofluorocarbons using an extraction agent such as trichloroethylene or perchloroethylene, among others. U.S. Pat. No. 5,211,817 attempts a separation of fluorocarbons from azeotropic mixtures with HF by column distillation and withdrawing a vapor side-stream followed by introducing the side-stream into a rectifying column equipped with a condenser and operated at a high reflux ratio. These provide less than satisfactory solutions to the problem.

It has now be found that individual halocarbons can be independently separated from a composition of two different halocarbons by freezing the composition at a temperature at or below the freezing point of the first halocarbon but above the freezing point of the second halocarbon.

HCFC-244bb and HCFO-1233xf are inseparable using conventional separation techniques known in the art since HCFC-244bb and HCFO-1233xf form a binary azeotrope or azeotrope-like composition which is described in U.S. Provisional Application 61/040,759 filed Mar. 31, 2008, the specification of which is incorporated herein by reference. It has been found that HCFC-244bb freezes at a temperature of about −78° C. while HCFO-1233xf does not freeze at this temperature. When it is desired to separate HCFC-244bb from HCFO-1233xf, the mixture of HCFC-244bb and HCFO-1233xf can be cooled to a temperature below the freezing point of HCFC-244bb but above the freezing point of HCFO-1233xf and then the two compounds can be separated by removing liquid or gaseous HCFO-1233xf from solid HCFC-244bb by decantation, filtration, use of centrifuge, or other means known in the art. Essentially pure HCFC-244bb and HCFO-1233xf can be recovered.

SUMMARY OF THE INVENTION

The invention provides a method for isolating a first halocarbon from a composition comprising a first halocarbon and at least one second halocarbon which is different from the first halocarbon, the method comprising cooling a composition comprising a first halocarbon and at least one second halocarbon at or below the freezing point of the first halocarbon but above the freezing point of the at least one second halocarbon.

The invention also provides a method for the production of 2,3,3,3-tetrafluoropropene which comprises (i) continuously reacting 2-chloro-3,3,3-trifluoropropene with hydrogen fluoride, in a liquid phase reaction, in the presence of a liquid phase fluorination catalyst to produce a composition comprising unreacted HF, unreacted 2-chloro-3,3,3-trifluoropropene, and 2-chloro-1,1,1,2-tetrafluoropropane; and then (ii) isolating an azeotrope or azeotrope-like composition of 2-chloro-1,1,1,2-tetrafluoropropane and 2-chloro-3,3,3-trifluoropropene; and then (iii) isolating 2-chloro-1,1,1,2-tetrafluoropropane from the azeotrope or azeotrope-like composition by cooling the azeotrope or azeotrope-like composition at or below the freezing point of 2-chloro-1,1,1,2-tetrafluoropropane but above the freezing point of 2-chloro-3,3,3-trifluoropropene; and then (iv) dehydrochlorinating the isolated 2-chloro-1,1,1,2-tetrafluoropropane under conditions effective to produce 2,3,3,3-tetrafluoropropene; and (v) optionally, recycling the isolated 2-chloro-3,3,3-trifluoropropene back to the reaction of step (i).

DETAILED DESCRIPTION OF THE INVENTION

In the process of the instant invention, one commences with a mixture of a first halocarbon and at least one second halocarbon. The mixture may be an azeotrope, but this condition is not necessary. The thermodynamic state of a fluid is defined by its pressure, temperature, liquid composition and vapor composition. For a true azeotropic composition, the liquid composition and vapor phase are essentially equal at a given temperature and pressure. In practical terms this means that the components cannot be separated during a phase change. For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which mean compositions that behave like azeotropes, i.e., have constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The first halocarbon and at least one second halocarbon in the composition may each independently be a fluorocarbon (FC), a hydrofluorocarbon (HFC), a hydrofluoroolefin (HFO), a chlorocarbon (CC), a hydrochlorocarbon (HCC), fluorochlorocarbon (FCC), a hydrochlorofluorocarbon (HCFC), a hydrofluoroether (HFE), or a hydrochlorofluoroolefin (HCFO), provided that the second halocarbon is a different from the first halocarbon. In one embodiment, the first halocarbon and the at least one second halocarbon form an azeotrope or azeotrope-like composition. In another embodiment the first halocarbon and the second halocarbon do not form an azeotrope or azeotrope-like composition. As examples, the first halocarbon and at least one second halocarbon in the composition may each independently be a compound of the Formula (I) and/or Formula (II), provided the first halocarbon and the at least one second halocarbon are different, and the freezing point of the first halocarbon is above the freezing point of the at least one second halocarbon.

Formula (I)—is a haloalkane having the formula $C_yH_zX$, wherein $X=F_aCl_bBr_cI_d$ having one or more halogen atoms, or a combination of different halogen atoms independently selected from F, Cl, Br, I with the total number of halogen atoms equals to $2y+2-z$; y is an integer of from 1 to 4; and z is an integer of from 0 to 9 such that $z=2y+1$; a, b, c, d are each an integer of from 1 to 10 and wherein $a+b+c+d=2y+2-z$. Formula (II)—is a haloalkene having the formula $C_yH_zX$, where $X=F_aCl_bBr_cI_d$ one or more halogen atoms, or a combination of different halogen atoms independently selected from F, Cl, Br, I with the total number of halogen atoms equals to $2y-z$; y is an integer of from 1 to 4; and z is an integer of from 0 to 7 such that z ranges from 0 to $2y-1$; a, b, c, d are each an integer of from 1 to 8 and wherein $a+b+c+d=2y-z$.

Non-limiting examples of halocarbons include 2-chloro-1,1,1,2-tetrafluoropropane (HCFC-244bb); 2-chloro-3,3,3-trifluoropropene (HCFO-1233xf), trans 1,2-dichloroethylene, pentafluorobutane; pentafluoropropane; hexafluoropropane; and heptafluoropropane; 1-chloro-1,2,2,2-tetrafluoroethane (HCFC-124); and pentafluoroethane (HFC-125); as well as 1,1-dichloro-1-fluoroethane (HCFC-141b) 1,1,2,2-tetrafluoroethane (HFC-134); 1,1,1,2-tetrafluoroethane (HFC-134a); 1-chloro 1,1-difluoroethane (HCFC-142b); 1,1,1-trifluoroethane (HFC-143a); 1,1-dichloro-2,2,2-trifluoroethane (HCFC-123); 1,2-dichloro-1,2,2-trifluoroethane (HCFC-123a); 1,1,1,3,3-pentafluorobutane (HFC-365mfc); 1,1,1,2,3,3,3-heptafluoropropane (HCF-227ea); trichlorofluoromethane (CFC-1), dichlorodifluoromethane (CFC-12); 1,1,1,3,3,3-hexafluoropropane (HFC-236fa); 1,1,1,2,3,3-hexafluoropropane (HFC-236ea); difluoromethane (HFC-32); chlorofluoromethane (HCFC-31); difluoroethane (HFC-152a); 1,1,1,3,3-pentafluoropropane (HFC-245fa); 1,1,1,2,3-pentafluoropropane (HFC-245eb); 1,1,1,2,2-pentafluoropropane (HFC-245cb), trifluoropropenes, pentafluoropropenes, chlorotrifluoropropenes, hydrofluoroethers, and tetrafluoropropenes including 1,3,3,3-tetrafluoropropene (HFO-1234ze), 2,3,3,3-tetrafluoropropene (HFO-1234yf), 1,2,3,3,3-pentafluoropropene (HFO-1225ye), and 1-chloro-3,3,3-trifluoropropene (HCFC-1233zd).

The present invention provides a composition which comprises effective amounts of a first halocarbon and at least one second halocarbon. By effective amount is meant an amount of each component which, when combined with the other component, results in the formation of a homogeneous mixture, and preferably an azeotropic or azeotrope-like composition. In one embodiment the compositions preferably are binary azeotropes which consist essentially of combinations of only the first halocarbon and a second halocarbon.

In one embodiment, the composition contains from about 1 to about 99 weight percent of the first halocarbon, preferably from about 1 weight percent to about 50 weight percent of the first halocarbon based on the weight of the overall composition. In one embodiment, the composition contains from about 1 to about 99 weight percent of the second halocarbon, preferably from about 50 weight percent to about 99 weight percent of at least one second halocarbon based on the weight of the overall composition.

After a mixture of first halocarbon and the at least one second halocarbon is separated from impurities, the mixture can be cooled to the temperature below the freezing point of the first halocarbon but above the freezing point of the at least one second halocarbon. In one embodiment a temperature difference between the freezing point of the first halocarbon and the freezing point of the second halocarbon is about 3° C. or more. In one embodiment the cooling is conducted at a temperature of from about −150° C. to about 75° C. In another embodiment the cooling is conducted at a temperature of from about −130° C. to about 50° C. In another embodiment the cooling is conducted at a temperature of from about −120° C. to about 25° C. The result of the cooling is the first halocarbon in solid form and the second halocarbon in liquid or gaseous form. A preferred step comprises the subsequent step of separating the liquid or gaseous second halocarbon from the solid first halocarbon. Essentially pure solid first halocarbon can be recovered by decantation, filtration, centrifugation, degassation under vacuum or by other means known in the art.

In one particularly preferred embodiment, the first halocarbon is 2-chloro-1,1,1,2-tetrafluoropropane (HCFC-244bb)

and the second halocarbon is 2-chloro-3,3,3-trifluoropropene (HCFO-1233xf) and wherein these form an azeotrope or azeotrope-like composition.

In a method of preparing a HCFC-244bb precursor, reagents are fluorinated with hydrogen fluoride. This may be done, for example, by the liquid phase or gas phase catalytic fluorination of $CF_3CCl=CH_2$ (HCFO-1233xf) with HF to yield HCFC-244bb. The reaction products of such precursors include HCFC-244bb, unreacted HCFO-1233xf, unreacted HF and other by-products. Upon removal of the by-products and HF, a binary azeotrope or azeotrope-like composition of HCFC-244bb and HCFO-1233xf is formed as disclosed in U.S. Provisional Application 61/040,759 filed Mar. 31, 2008. This binary azeotrope or azeotrope-like composition is then available for separation into its component parts by the method of this invention. Then essentially pure HCFC-244bb can be fed into a dehydrochlorination reactor to make HFO-1234yf and essentially pure HCFO-1233xf can optionally be recycled back to a fluorination reactor to produce HCFC-244bb.

After a mixture of HCFC-244bb and HCFO-1233xf is separated from impurities, the mixture can be cooled to the temperature below the freezing point of HCFC-244bb (about −78° C., the temperature of acetone and dry ice) but above the freezing point of HCFO-1233xf. The result of the cooling is solid HCFC-244bb and liquid or gaseous HCFO-1233xf. Then essentially pure solid HCFC-244bb can be recovered by decantation, filtration, centrifugation, degassation under vacuum or by other means known in the art.

In one embodiment, the mixture of HCFC-244bb and HCFO-1233xf is injected into a vessel maintained at temperature from about from about −85° C. to about −75° C.; preferably from about −81° C. to about −78° C. Then HCFO-1233xf is removed from the vessel by filtration. After heating the vessel to the temperature above freezing point of HCFC-244bb essentially pure liquid HCFC-244bb can be recovered.

In another embodiment, the mixture of HCFC-244bb and HCFO-1233xf is injected into a vessel maintained at temperature from about −81° C. to about −78° C. Then essentially HCFC-244bb is separated from essentially pure liquid HCFO-1233xf using a centrifuge.

In one preferred embodiment, the invention relates to a multistep process in which the above described process to isolate HCFC-244bb from HCFO-1233xf is preceded by a prior process step for producing 2-chloro-1,1,1,2-tetrafluoropropane (HCFC-244bb) by liquid phase fluorination of 2-chloro-3,3,3-trifluoropropene (HCFO-1233xf) with hydrogen fluoride to produce a stream comprising hydrogen fluoride, 2-chloro-1,1,1,2-tetrafluoropropane, and 2-chloro-3,3,3-trifluoropropene.

In the practice of the present invention, a liquid phase catalyst as described below is charged into a fluorination reactor prior to heating the reactor. Any reactor suitable for a fluorination reaction may be used in the invention. Preferably the reactor is constructed from materials which are resistant to the corrosive effects of HF such as Hastelloy-C, Inconel, Monel and fluoropolymer-lined vessels. Such liquid phase fluorination reactors are well known in the art. Then the HF and HCFO-1233xf are fed to the reactor after the reactor reaches the desired temperature. In the preferred embodiment, the reaction is conducted at a temperature of from about 30° C. to about 200° C., more preferably from about from about 50° C. to about 150° C., and still more preferably from about 75° C. to about 125° C. The pressure of the reaction varies depending on the temperature, quantity of hydrogen chloride and hydrogen fluoride used, and conversion of HCFO-1233xf. Convenient operating pressure ranges from about 5 psia to about 200 psia, and preferably from 30 to about 175 psia, and most preferably about 60 psia to about 150 psia.

In the preferred embodiment, the catalyst is present in an amount of from about 2% to about 80%, and preferably from about 5% to about 50%, and most preferably from about 10% to about 20%, based on the mole percent of HCFO-1233xf. Fluorination catalysts having a purity of at least 98% are preferred.

Based on reaction stoichiometry, the required mole ratio of HF to HCFO-1233xf is at least equal to the number of double bonds in the starting organic material and preferably is present in an excess. In the preferred embodiment, the mole ratio of HF to HCFO-1233xf ranges from at least about 1:1 to about 50:1, more preferably from about 1:1 to about 30:1 and most preferably from about 2:1 to about 15:1. Any water in the HF will react with and deactivate the catalyst. Therefore substantially anhydrous HF is preferred. By "substantially anhydrous" is meant that the HF contains less than about 0.05 weight % water and preferably contains less than about 0.02 weight % water. However, one of ordinary skill in the art will appreciate that the presence of water in the catalyst can be compensated for by increasing the amount of catalyst used. HF suitable for use in the reaction may be purchased from Honeywell International Inc. of Morristown, N.J.

Any liquid phase fluorination catalyst may be used in the invention. A non-exhaustive list includes Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

The resulting HCFC-244bb and unreacted HCFO-1233xf can be recovered from the reaction mixture (HCFC-244bb, HCFO-1233xf, HF and impurities) via any separation or purification method known in the art such as neutralization and distillation. The HCFC-244bb is then isolated by the method of the present invention. HCFC-244bb in an essentially pure form is used as an intermediate in the production of 2,3,3,3-tetrafluoropropene HFO-1234yf. The process of the invention may be carried out either in a batch or continuous mode. In a continuous process, the HCFO-1233xf and HF are preferably fed simultaneously to the reactor after the reactor reaches the desired temperature. The temperature and pressure of the fluorination reaction remain essentially the same for both the batch and continuous modes of operation. The residence time or contact time, varies from about 1 second to about 2 hours, preferably from about 5 seconds to about 1 hour and most preferably from about 10 seconds to about 30 minutes. A sufficient quantity of catalyst must be present to affect the fluorination in the residence times described above. In a continuous mode of operation, HCFC-244bb, unreacted HCFO-1233xf, and unreacted HF are continuously removed from the reactor.

In a preferred embodiment, the invention relates to a multistep process in which the above described process to isolate HCFC-244bb from HCFO-1233xf is followed by a subsequent process step for producing 2,3,3,3-tetrafluoropropene (HFO-1234yf) by vapor or liquid phase dehydrochlorination of 2-chloro-1,1,1,2-tetrafluoropropane (HCFC-244bb) in the presence of a catalyst or caustic solution to produce a stream comprising 2,3,3,3-tetrafluoropropene and HCl.

The catalytic conversion of HCFC-244bb is conducted under conditions effective to dehydrochlorinate HCFC-244bb to produce 2,3,3,3-tetrafluoropropene (HFO-1234yf. Preferably dehydrochlorination of HCFC-244bb is done in a vapor phase, and more preferably in a fixed-bed reactor in the vapor phase. The dehydrochlorination reaction may be conducted in any suitable reaction vessel or reactor, but it should preferably be constructed from materials which are resistant to the corrosive effects of hydrogen chloride (to the extent that such material is formed under the dehydrochlorination conditions) such as nickel and its alloys, including Hastelloy, Inconel, Incoloy, and Monel or vessels lined with fluoropolymers and may employ single or multiple tubes packed with a dehydrochlorination catalyst.

Catalysts for HCFC-244bb Dehydrochlorination to HFO-1234yf.

The catalysts may be metal halides, halogenated metal oxides, neutral (or zero oxidation state) metal or metal alloy, or activated carbon in bulk or supported form. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

The HCFC-244bb is introduced into the reactor either in pure form, partially purified form, or as part of the reactor effluent from the preceding step. The HCFC-244bb may optionally be fed with an inert gas diluent such as nitrogen, argon, or the like. In a preferred embodiment of the invention, the HCFC-244bb is pre-vaporized or preheated prior to entering the reactor. Alternately, the HCFC-244bb is vaporized inside the reactor. Useful reaction temperatures may range from about 100° C. to about 700° C. Preferred temperatures may range from about 150° C. to about 600° C., and more preferred temperatures may range from about 200° C. to about 550° C. The reaction may be conducted at atmospheric pressure, super-atmospheric pressure or under vacuum. The vacuum pressure can be from about 5 torr (0.0966 psig) to about 760 torr (14.69 psig). Contact time of the HCFC-244bb with the catalyst may range from about 0.5 seconds to about 120 seconds, however, longer or shorter times can be used.

Preferably in such dehydrochlorination embodiments as described in this section, the conversion of the HCFC-244bb is at least about 10%, more preferably at least about 20%, and even more preferably at least about 30%. Preferably in such embodiments, the selectivity to HFO-1234yf, is at least about 70%, more preferably at least about 85% and more preferably at least about 95%.

In the preferred embodiment, the process flow is in the down or up direction through a bed of the catalyst. It may also be advantageous to periodically regenerate the catalyst after prolonged use while in place in the reactor. Regeneration of the catalyst may be accomplished by any means known in the art, for example, by passing air or air diluted with nitrogen over the catalyst at temperatures of from about 100° C. to about 400° C., preferably from about 200° C. to about 375° C., for from about 0.5 hour to about 3 days.

In general, the effluent from the dehydrochlorination reaction step, including any intermediate effluents that may be present in multi-stage reactor arrangements, may be processed to achieve desired degrees of separation and/or other processing. For example, in embodiments in which the reactor effluent comprises HFO-1234yf, the effluent will generally also include HCl and unreacted HCFC244bb. Some portion or substantially all of these components of the reaction product may be recovered from the reaction mixture via any separation or purification method known in the art such as neutralization and distillation. It is expected that unreacted HCFC-244bb could be recycled, completely or partially, to improve the overall yield of the desired $CF_3CF=CH_2$ (HFO-1234yf). Optionally, but preferably, hydrogen chloride is then recovered from the result of the dehydrochlorination reaction. Recovering of hydrogen chloride is conducted by conventional distillation where it is removed from the distillate.

Alternatively, HCl can be recovered or removed by using water or caustic scrubbers. When a water extractor is used HCl is removed as an aqueous solution. When caustic is used, HCl is just removed from system as a chloride salt in aqueous solution.

In an alternate embodiment of the invention, dehydrochlorination of HCFC-244bb can also be accomplished by reacting it with a strong caustic solution that includes, but is not limited to KOH, NaOH, $Ca(OH)_2$ and CaO at an elevated temperature. In this case, the strength of the caustic solution is of from about 2 wt % to about 100 wt %, more preferably from about 5 wt % to about 90 wt % and most preferably from about 10 wt % to about 80 wt %. The caustic to HCFC-244bb mole ratio preferably ranges from about 1:1 to about 2:1; more preferably from about 1.1:1 to about 1.5:1 and most preferably from about 1.2:1 to about 1.4:1. The reaction may be conducted at a temperature of from about 20° C. to about 100° C., more preferably from about 30° C. to about 90° C. and most preferably from about 40° C. to about 80° C. As above, the reaction may be conducted at atmospheric pressure, super-atmospheric pressure or under vacuum. The vacuum pressure can be from about 5 torr (0.0966 psig) to about 760 torr (14.69 psig). In addition, a solvent or phase transfer catalyst such as Aliquat 336 may optionally be used to help dissolve the organic compounds in the caustic solution. This optional step may be conducted using solvents that are well known in the art for said purpose. Thereafter, HFO-1234yf may be recovered from the reaction product mixture comprised of unreacted starting materials and by-products by any means known in the art, such as by extraction and preferably distillation. The mixture of HFO-1234yf and any by-products are passed through a distillation column. For example, the distillation may be preferably conducted in a standard distillation column at atmospheric pressure, super-atmospheric pressure or a vacuum. Preferably the pressure is less than about 300 psig, preferably less than about 150 psig and most preferably less than 100 psig. The pressure of the distillation column inherently determines the distillation operating temperature. Preferably in such dehydrochlorination embodiments as described in this section, the conversion HCFC-244bb is at least about 60%, more preferably at least about 75%, and even more preferably at least about 90%. Preferably in such embodiments, the selectivity to HFO-1234yf, is at least about 70%, more preferably at least about 85% and more preferably at least about 95%.

The following non-limiting examples serve to illustrate the invention.

Example 1

An ebulliometer comprising a vacuum jacketed tube with a condenser on top which is further equipped with a Quartz Thermometer is used. About 20.91 g HCFO-1233xf is charged to the ebulliometer and then HCFC-244bb is added in small, measured increments. Temperature depression is observed when HCFC-244bb is added to HCFO-1233xf, indicating a binary minimum boiling azeotrope is formed. From greater than about 0 to about 5 weight percent 244bb, the boiling point of the composition stays below or around the boiling point of 1233xf. The boiling temperature of HCFO-1233xf (98% pure) is about 9.82° C. at 14.4 psia, and the boiling of TOX grade HCFO-1233xf (99.99% pure) is about 12° C. at 14.5 psia. The boiling point of HCFC-244bb is about 14.0 at 14.5 psia. The binary mixtures shown in Table 1 were studied. The compositions exhibit azeotrope and/or azeotrope-like properties over this range.

TABLE 1

HCFO-1233xf/HCFC-244bb Compositions at P = 14.4 psia.

| T (° C.) | Wt. % HCFO-1233xf | Wt. % HCFC-244bb |
|---|---|---|
| 9.79 | 98.35 | 1.65 |
| 9.78 | 96.54 | 3.46 |
| 9.78 | 94.83 | 5.17 |
| 9.85 | 93.18 | 6.82 |
| 9.95 | 91.11 | 8.89 |
| 10.00 | 87.45 | 12.45 |
| 10.25 | 83.91 | 16.09 |
| 10.36 | 80.86 | 19.14 |
| 10.43 | 76.37 | 23.63 |

Example 2

The vapor pressure of pure HCFO-1233xf, HCFC-244bb and 50/50% mixture of HCFO-1233xf/HCFC-244bb was measured. The result in Table 2 shows that the vapor pressure of this mixture is higher than the vapor pressure of either pure component HCFO-1233xf, and HCFC-244bb at 0, 25 and 60° C.

TABLE 2

Vapor Pressure of HCFO-1233xf/HCFC-244bb mixture

| T (° C.) | Pressure (Psia) | Wt. % HCFO-1233xf/ HCFC-244bb |
|---|---|---|
| 0.0 | 8.87 | 100.0/0.0 |
| | 9.43 | 50.0/50.0 |
| | 8.24 | 0.0/100.0 |
| 25.0 | 22.88 | 100.0/0.0 |
| | 23.81 | 50.0/50.0 |
| | 21.33 | 0.0/100.0 |
| 60.0 | 64.58 | 100.0/0.0 |
| | 64.98 | 50.0/50.0 |
| | 59.75 | 0.0/100.0 |

Example 3

A 500 cm$^3$ Teflon cylinder was charged with 100 grams of HCFC-244bb. The cylinder was placed into the Dewar filled with Acetone and Dry Ice mixture (temperature about −78° C.). After 1 hour the cylinder was removed from the Dewar and HCFC-244bb was observed to be frozen.

Example 4

A 500 cm$^3$ Teflon cylinder was charged with 81 grams of HCFC-244bb and HCFO-1233xf mixture. The cylinder was placed into the Dewar filled with Ethanol and Dry Ice mixture (temperature about −78° C.). After 1 hour the cylinder was removed from the Dewar and a liquid layer was observed on top of a solid layer. The cylinder was then placed into the cold bath for an additional 1 hour. Then the liquid was transferred into an empty evacuated cylinder. GC analysis of this liquid showed that it was enriched in HCFO-1233xf relative to the initial mixture charged into the Teflon cylinder.

Example 5

A filtration vessel equipped with a cooling system is charged with a HCFC-244bb and HCFO-1233xf mixture. The vessel is cooled to about −78° C. to −85° C. and essentially pure HCFC-244bb is then recovered by removing HCFO-1233xf from the vessel by filtration.

Example 6

A 500 cm$^3$ stainless steel cylinder is charged with 100 grams of refrigerant R410A which is a 50/50 wt % azeotropic mixture of pentafluoroethane (HFC-125) (FP=−103° C.) and difluoromethane (HFC-32) (FP=−136° C.). The cylinder is placed into a low temperature chamber that is capable of achieving a temperature about that of liquid nitrogen (−196° C.). The chamber is equipped with a temperature control system using liquid N$_2$ as the coolant. The cylinder is cooled to about −110° C. which freezes the HFC-125 component of the mixture. Then the liquid portion of the sample is transferred into an empty evacuated cylinder. GC analysis of this liquid shows that it is highly enriched in HFC-32 relative to the initial mixture charged into the cylinder.

Example 7

A 500 cm$^3$ stainless steel cylinder is charged with 200 grams of refrigerant R407c which is a ternary mixture of HFC-32 (FP=−136° C.)/HFC-125 (FP=−103° C.)/HFC-134a (FP=−101° C.). The composition of the mixture is 38/18/44 mole % respectively. The cylinder is placed into the same low temperature chamber as in Example 6. The cylinder is cooled to about −110° C. which freezes the HFC-125 and HFC-134a components of the mixture. Then the liquid portion of the sample is transferred into an empty evacuated cylinder. GC analysis of this liquid shows that it is highly enriched in HFC-32 relative to the initial mixture charged into the cylinder.

Example 8

This example illustrates the continuous liquid phase hydrofluorination reaction of 2-chloro-3,3,3-trifluoropropene (HCFO-1233xf)+HF→2-chloro-1,1,1,2-tetrafluoropropane (HCFC-244bb)

About 4255 grams of $SbCl_5$ were contained in a Teflon™-lined liquid phase reactor (Teflon is a trademark of E.I. duPont de Nemours & Co) equipped with a 2-inch ID (inside diameter) packed column and a condenser. The reactor was 2.75-inch ID×36-inch L (length). Initially, a greater than 5:1 mole ratio of HF was added to the reactor to fluorinate the catalyst. A greater than 3:1 mole ratio of $Cl_2$ was then added to the reactor to ensure that the catalyst was brought back to a pentavalent state. The reactor was heated to about 85° C.-87° C. HF feed was started first. After about 1.5 lbs of HF had been added, the 2-chloro-3,3,3-trifluoropropene feed was started. The purity of the 2-chloro-3,3,3-trifluoropropene feed stock was about 97.3 GC area %. The experiment ran continuously for 71 hours. For this run, $Cl_2$ was fed batchwise about every 4 hours throughout the run to keep the catalyst active.

The experiment was run for a total of 38.75 hours. A total of 45.1 pounds of HCFO-1233xf was fed during the run. For the first 11.75 hours the average HCFO-1233xf feed rate was 0.62 lb/hr and the HF feed rate averaged 0.73 lb/hr. This is a mole ratio of HF to HCFO-1233xf of 7.7 to 1. The feed rates were increased to an average of 1.38 lb/hr of HCFO-1233xf and 1.53 lb/hr of HF for the next 16.25 hours. This is a mole ratio of HF to HCFO-1233xf of 7.2 to 1. The organic feed was reduced slightly for the next 11.75 hrs to an average of 1.31 lb/hr. The HF feed rate stayed the same as the previous 16.25 hours of on-stream time. The mole ratio of HF to HCFO-1233xf increased to 7.6 to 1.

For the first 11.75 hours the HCFO-1233xf conversion on a molar basis averaged 97.6% excluding the $1^{st}$ couple of samples (before steady state was achieved). The selectivity (molar basis) of HCFC-244bb averaged 97.1%.

For the next 16.25 hours the HCFO-1233xf conversion on a molar basis averaged 88.9% and the selectivity (molar basis) of HCFC-244bb averaged 95.8%. During this time the $Cl_2$ addition frequency was increased from adding every 4 hr to once every 3 hr. This had no effect on the HCFO-1233xf conversion or the 244bb selectivity which leads one to believe that the 3-4 wt % $Cl_2$ to organic ratio that was chosen is sufficient to keep the catalyst active and adding extra $Cl_2$ (adding it more frequently) only adds to an increase in the amount of HCFO-1223xd for some period of time after the $Cl_2$ addition.

Finally, for the last 11.75 hours the HCFO-1233xf conversion on a molar basis averaged 92.3% and the selectivity (molar basis) of HCFC-244bb averaged 96.4%.

The reactor temperature range for the experiment was 78° C.-86° C. and the pressure range was 70 psig-105 psig. The organic crude material collected from the run was run on a gas chromatograph and exhibited the following GC analysis. The following Table 3 sets forth the 2-chloro-3,3,3-trifluoropropene (HCFO-1233xf) conversion and product selectivity data.

TABLE 3

(Conversion and Selectivity on a Molar Basis)

| hours elapsed Time | Temp (° C.) | molar selectivity HFC-245cb | molar selectivity HCFC-244bb | molar Conversion % HCFO-1233xf | molar selectivity HCFC-235da | molar selectivity HCFO-1223xd | molar selectivity others |
|---|---|---|---|---|---|---|---|
| 1 | 84.1 | 8.6 | 87.6 | 94.5 | 0.0 | 0.2 | 3.6 |
| 2 | 85 | 1.3 | 98.3 | 93.8 | 0.0 | 0.0 | 0.3 |
| 4 | 85.2 | 0.6 | 96.5 | 94.8 | 0.0 | 1.0 | 1.9 |
| 5 | 85.6 | 4.3 | 90.8 | 92.6 | 0.0 | 0.6 | 4.3 |
| 6 | 83.6 | 1.3 | 93.1 | 90.7 | 0.0 | 0.8 | 4.7 |
| 8 | 85.5 | 2.1 | 95.6 | 93.3 | 0.0 | 0.4 | 1.9 |
| 9 | 86.9 | 2.1 | 95.9 | 95.5 | 0.0 | 0.2 | 1.7 |
| 11 | 83 | 0.5 | 81.6 | 95.6 | 0.6 | 2.8 | 14.5 |
| 12 | 85.9 | 3.9 | 93.7 | 90.2 | 0.1 | 0.3 | 1.9 |
| 13 | 85.3 | 0.9 | 87.2 | 93.1 | 1.6 | 3.0 | 7.3 |
| 14 | 83.1 | 3.0 | 94.5 | 95.4 | 0.4 | 0.7 | 1.4 |
| 15 | 80 | 1.3 | 95.4 | 87.5 | 0.9 | 1.0 | 1.5 |
| 16 | 81.7 | 3.1 | 95.8 | 77.8 | 0.3 | 0.2 | 0.6 |
| 17 | 81.3 | 1.5 | 96.3 | 79.5 | 0.4 | 0.4 | 1.3 |
| 18 | 84.1 | 11.1 | 87.0 | 83.9 | 0.1 | 0.1 | 1.6 |
| 19 | 85 | 2.3 | 96.9 | 87.7 | 0.1 | 0.2 | 0.4 |
| 20 | 85.2 | 9.9 | 87.7 | 88.5 | 0.3 | 0.1 | 2.0 |
| 23 | 86.4 | 2.0 | 96.8 | 90.6 | 0.2 | 0.4 | 0.6 |
| 25 | 83.2 | 1.1 | 97.7 | 89.8 | 0.4 | 0.4 | 0.3 |
| 26 | 85.5 | 4.4 | 94.5 | 90.5 | 0.0 | 0.3 | 0.8 |
| 27 | 85.7 | 1.9 | 97.3 | 89.4 | 0.2 | 0.3 | 0.3 |
| 28 | 83.5 | 2.6 | 96.8 | 82.8 | 0.1 | 0.2 | 0.3 |
| 30 | 80.7 | 2.0 | 97.0 | 80.5 | 0.0 | 0.3 | 0.7 |
| 32 | 84.3 | 0.5 | 97.8 | 85.6 | 0.2 | 0.6 | 1.0 |
| 33 | 81.9 | 3.4 | 95.8 | 85.1 | 0.1 | 0.1 | 0.5 |
| 34 | 84.1 | 1.8 | 96.5 | 77.8 | 0.5 | 0.6 | 0.6 |
| 35 | 85.6 | 1.4 | 97.2 | 75.0 | 0.4 | 0.4 | 0.6 |
| 36 | 85.2 | 1.0 | 97.9 | 76.6 | 0.6 | 0.2 | 0.3 |
| 37 | 84.9 | 0.7 | 96.3 | 76.1 | 0.9 | 0.3 | 1.8 |
| 38 | 84.0 | 1.5 | 96.3 | 79.5 | 0.4 | 0.4 | 1.3 |

Example 9

This example illustrates the continuous vapor phase dehydrochlorination reaction of 2-chloro-1,1,1,2-tetrafluoropropane (HCFC-244bb)→2,3,3,3-tetrafluoropropene (HFO-1234yf)+HCl. The dehydrochlorination catalyst was 10 wt % CsCl/90 wt % $MgF_2$.

Conversion of HCFC-244bb into HFO-1234yf was performed using Monel reactor (ID 2 inch, length 32 inch) equipped with a Monel preheater (ID 1 inch, length 32 inch) which was filled with Nickel mesh to enhance heat transfer. The reactor was filled with 2.0 L of pelletized 10 wt % CsCl/90 wt % $MgF_2$ dehyrochlorination catalyst. Nickel mesh was placed at the top and at the bottom of reactor to support the catalyst. Multi-point thermocouple was inserted at the center of the reactor. The catalyst was pretreated in dry N2 flow for 6 hours at the temperature of 480° C. Then the feed with the composition 95GC % 244bb/3.1GC % 1233xf/0.35GC % 245cb was introduced into the reactor at the rate of 1.0 lb/hr. The feed was vaporized prior entering the reactor preheater. The bottoms of the distillation column were discharged and recycled into the reactor. The feed rate was maintained constant at 1.0 lbs/hr and both temperature and pressure were varied. Temperature gradient throughout the reactor was within about 3-5° C. The productivity of the catalyst was estimated at 3-6 lbs/hr/ft³. The highest productivity was observed at 470° C. and 45 psig, and the lowest productivity was observed at 480° C. and 3 psig pressure. The reaction products were fed into the caustic scrubber to remove HCl by-product. Then the product stream was passed through a column filled with desiccant to remove residual moisture. Oil-less compressor was used to feed crude product into the distillation column that was maintained at 30-45 psig pressure. Distillation was performed in a continuous mode and the take-off rate was equal to the rate of production of HFO-1234yf in the reactor. The purity of distilled 1234yf was 99.9GC %+GC analysis of the distillate showed presence of light impurities with a ppm level of heavy impurities. The following conversions and selectivities were achieved:

480° C. at 3 psig—HCFC-244bb conversion~30%, Selectivity to HFO-1234yf~97%

480° C. at 20 psig—HCFC-244bb conversion~47%, Selectivity to HFO-1234yf~96%

470° C. at 20 psig—HCFC-244bb conversion~36%, Selectivity to HFO-1234yf~97%

470° C. at 45 psig—HCFC-244bb conversion~53%, Selectivity to HFO-1234yf~96%

460° C. at 45 psig—HCFC-244bb conversion~38%, Selectivity to HFO-1234yf~98%

Reaction data.
Conditions: Feed 95GC % HCFC-244bb/3.1GC % HCFO-1233xf/0.35GC % HFC-245cb; 2.0 L of 10 wt % CsCl/90 wt % $MgF_2$ catalyst; 1.0 lb/hr feed rate.

| Time on-stream (hrs.) | Conversion of HCFC-244bb (%) | Selectivity to HFO-1234yf (%) | Temperature (° C.) | Pressure (psig) |
|---|---|---|---|---|
| 0.25 | 93.30 | 82.42 | 484.30 | 3.00 |
| 0.80 | 67.61 | 90.38 | 489.00 | 3.90 |
| 1.43 | 47.78 | 94.14 | 479.80 | 3.50 |
| 2.27 | 31.98 | 97.34 | 479.80 | 3.40 |
| 3.32 | 29.36 | 97.70 | 478.80 | 3.80 |
| 4.32 | 26.24 | 97.56 | 478.70 | 2.80 |
| 5.23 | 28.45 | 97.88 | 480.30 | 2.90 |
| 6.20 | 30.53 | 98.01 | 480.30 | 3.20 |
| 6.80 | 30.91 | 98.13 | 478.40 | 3.30 |
| 7.37 | 28.36 | 97.88 | 478.80 | 2.90 |
| 7.93 | 29.01 | 97.84 | 479.30 | 3.10 |
| 8.48 | 29.95 | 97.91 | 478.30 | 3.30 |
| 9.05 | 26.61 | 96.76 | 479.60 | 2.70 |
| 9.62 | 27.98 | 96.12 | 476.80 | 2.90 |
| 10.20 | 28.84 | 96.66 | 480.20 | 3.00 |
| 10.70 | 29.70 | 97.16 | 480.50 | 3.10 |
| 11.22 | 29.30 | 97.62 | 480.30 | 3.30 |
| 11.72 | 30.47 | 97.65 | 480.70 | 3.30 |
| 12.25 | 29.57 | 97.59 | 480.30 | 3.30 |
| 12.75 | 29.83 | 97.92 | 480.00 | 3.50 |
| 13.27 | 30.10 | 98.23 | 479.60 | 2.80 |
| 13.78 | 28.73 | 97.02 | 480.10 | 2.80 |
| 14.28 | 29.54 | 97.31 | 480.80 | 2.90 |
| 14.80 | 29.95 | 98.05 | 479.80 | 2.90 |
| 15.30 | 29.71 | 97.98 | 480.60 | 3.00 |
| 15.80 | 30.50 | 98.14 | 480.80 | 2.90 |
| 16.32 | 30.68 | 97.96 | 481.50 | 3.10 |
| 16.83 | 32.21 | 97.79 | 482.50 | 3.10 |
| 17.35 | 30.37 | 97.68 | 478.00 | 3.20 |
| 17.85 | 27.67 | 97.18 | 479.20 | 3.30 |
| 18.40 | 28.06 | 96.50 | 477.50 | 3.20 |
| 18.95 | 27.84 | 96.58 | 478.20 | 3.40 |
| 19.50 | 28.85 | 96.66 | 482.30 | 3.40 |
| 20.18 | 32.52 | 97.55 | 480.00 | 3.40 |
| 20.87 | 29.15 | 97.47 | 480.10 | 3.20 |
| 22.90 | 64.16 | 97.20 | 478.90 | 17.40 |
| 23.65 | 47.32 | 96.23 | 477.80 | 17.50 |
| 24.32 | 47.80 | 96.81 | 478.60 | 17.00 |
| 25.00 | 47.45 | 96.83 | 479.40 | 16.90 |
| 26.02 | 47.10 | 96.84 | 479.50 | 18.50 |
| 26.78 | 46.99 | 97.34 | 478.60 | 20.00 |
| 27.38 | 48.61 | 97.45 | 478.80 | 20.00 |
| 28.22 | 47.00 | 97.41 | 477.80 | 20.00 |
| 28.93 | 48.53 | 96.40 | 480.00 | 20.00 |
| 29.63 | 46.61 | 96.10 | 477.70 | 20.00 |
| 30.23 | 49.28 | 96.14 | 480.80 | 20.00 |
| 30.83 | 44.30 | 96.11 | 477.70 | 20.00 |
| 31.45 | 48.53 | 96.18 | 479.50 | 20.00 |
| 32.05 | 45.03 | 97.45 | 477.70 | 20.00 |
| 32.72 | 48.94 | 97.09 | 480.10 | 20.00 |
| 33.30 | 45.10 | 96.24 | 478.00 | 20.00 |
| 33.83 | 46.72 | 96.25 | 479.70 | 20.00 |
| 34.37 | 49.04 | 96.21 | 479.30 | 20.00 |
| 34.90 | 46.86 | 96.34 | 477.80 | 20.00 |
| 35.42 | 41.57 | 97.52 | 474.60 | 20.00 |
| 35.95 | 38.83 | 97.44 | 469.40 | 20.00 |
| 36.48 | 31.20 | 97.45 | 468.40 | 20.00 |
| 37.02 | 34.86 | 96.45 | 470.10 | 20.00 |
| 37.55 | 35.41 | 96.44 | 470.20 | 20.00 |
| 38.07 | 37.17 | 97.71 | 469.90 | 20.00 |
| 38.63 | 36.72 | 97.31 | 471.10 | 20.00 |
| 39.15 | 36.66 | 97.68 | 470.00 | 20.00 |
| 39.67 | 37.41 | 97.85 | 470.80 | 20.00 |
| 40.20 | 36.43 | 97.86 | 469.40 | 20.00 |
| 40.73 | 36.10 | 97.98 | 469.20 | 20.00 |
| 41.27 | 35.34 | 97.97 | 470.50 | 20.00 |
| 42.05 | 37.63 | 96.08 | 472.00 | 20.00 |
| 42.57 | 38.60 | 97.20 | 470.30 | 20.00 |
| 43.12 | 57.72 | 96.75 | 469.60 | 45.00 |
| 43.65 | 53.72 | 95.42 | 467.10 | 45.00 |
| 44.17 | 51.28 | 94.83 | 468.70 | 45.00 |
| 44.68 | 51.60 | 96.39 | 467.50 | 45.00 |
| 45.20 | 52.52 | 96.36 | 469.80 | 45.00 |
| 45.72 | 53.43 | 96.5 | 468.90 | 45.00 |
| 46.77 | 51.14 | 95.44 | 468.50 | 45.00 |
| 48.15 | 53.38 | 97.23 | 470.70 | 45.00 |
| 49.32 | 54.53 | 97.21 | 470.90 | 45.00 |
| 50.88 | 51.94 | 97.21 | 469.40 | 45.00 |
| 52.35 | 39.24 | 97.70 | 459.60 | 45.00 |

-continued

Reaction data.
Conditions: Feed 95GC % HCFC-244bb/3.1GC % HCFO-
1233xf/0.35GC % HFC-245cb; 2.0 L of 10 wt %
CsCl/90 wt % MgF$_2$ catalyst; 1.0 lb/hr feed rate.

| Time on-stream (hrs.) | Conversion of HCFC-244bb (%) | Selectivity to HFO-1234yf (%) | Temperature (° C.) | Pressure (psig) |
|---|---|---|---|---|
| 53.75 | 39.15 | 97.19 | 459.30 | 45.00 |
| 55.03 | 38.45 | 97.63 | 458.30 | 45.00 |
| 56.57 | 37.19 | 97.61 | 457.50 | 45.00 |
| 57.85 | 37.44 | 97.88 | 458.90 | 45.00 |
| 58.93 | 38.18 | 97.91 | 458.80 | 45.00 |
| 59.98 | 37.98 | 98.04 | 460.10 | 45.00 |
| 61.05 | 39.77 | 97.43 | 463.00 | 45.00 |
| 62.10 | 42.11 | 97.92 | 462.20 | 45.00 |
| 63.20 | 41.11 | 97.74 | 459.10 | 45.00 |
| 64.27 | 39.64 | 98.05 | 460.60 | 45.00 |
| 65.32 | 40.98 | 97.70 | 461.40 | 45.00 |

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above, and all equivalents thereto.

What is claimed is:

1. A method for isolating a first halocarbon from a composition comprising a first halocarbon and at least one second halocarbon which is different from the first halocarbon, the method comprising:
   cooling a composition comprising a first halocarbon and at least one second halocarbon at or below the freezing point of the first halocarbon but above the freezing point of the at least one second halocarbon and
   recovering the first halocarbon from the at least one second halocarbon,
   wherein the first halocarbon is a compound of the Formula (I) or Formula (II), and the at least one second halocarbon is a different compound of the Formula (I) or Formula (II) wherein:
   Formula (I) is a haloalkane having the formula $C_yH_zX$, wherein $X=F_aCl_bBr_cI_d$ having one or more halogen atoms, or a combination of different halogen atoms independently selected from F, Cl, Br, I with the total number of halogen atoms equals to $2y+2-z$; y is an integer of from 1 to 4; and z is an integer of from 0 to 9 such that $z=2y+1$; a, b, c, d are each an integer of from 1 to 10 and wherein $a+b+c+d=2y+2-z$; and
   Formula (II) is a haloalkene having the formula $C_yH_zX$, where $X=F_aCl_bBr_cI_d$ one or more halogen atoms, or a combination of different halogen atoms independently selected from F, Cl, Br, I with the total number of halogen atoms equals to $2y-z$; y is an integer of from 1 to 4; and z is an integer of from 0 to 7 such that z ranges from 0 to $2y-1$; a, b, c, d are each an integer of from 1 to 8 and wherein $a+b+c+d=2y-z$.

2. The method of claim 1 wherein the first halocarbon and the different second halocarbon are each selected from 2-chloro-1,1,1,2-tetrafluoropropane; 2-chloro-3,3,3-trifluoropropene, trans 1,2-dichloroethylene, pentafluorobutane; pentafluoropropane; hexafluoropropane; heptafluoropropane; 1-chloro-1,2,2,2-tetrafluoroethane; and pentafluoroethane; 1,1-dichloro-1-fluoroethane (HCFC-141b) 1,1,2,2-tetrafluoroethane; 1,1,1,2-tetrafluoroethane; 1-chloro 1,1-difluoroethane; 1,1,1-trifluoroethane; 1,1-dichloro-2,2,2-trifluoroethane; 1,2-dichloro-1,2,2-trifluoroethane; 1,1,1,3,3-pentafluorobutane; 1,1,1,2,3,3,3-heptafluoropropane; trichlorofluoromethane, dichlorodifluoromethane; 1,1,1,3,3,3-hexafluoropropane; 1,1,1,2,3,3-hexafluoropropane; difluoromethane; chlorofluoromethane; difluoroethane; 1,1,1,3,3-pentafluoropropane (HFC-245fa); 1,1,1,2,3-pentafluoropropane; 1,1,1,2,2-pentafluoropropane, trifluoropropenes, pentafluoropropenes, chlorotrifluoropropenes, hydrofluoroethers, and tetrafluoropropenes including 1,3,3,3-tetrafluoropropene, 2,3,3,3-tetrafluoropropene, 1,2,3,3-pentafluoropropene, and 1-chloro-3,3,3-trifluoropropene.

3. The method of claim 1 wherein the first halocarbon and the at least one second halocarbon form an azeotrope or azeotrope-like composition.

4. The method of claim 1 wherein the first halocarbon and the at least one second halocarbon do not form an azeotrope or azeotrope-like composition.

5. The method of claim 1 wherein a temperature difference between the freezing point of the first halocarbon and the freezing point of the at least one second halocarbon is about 3° C. or more.

6. The method of claim 1 wherein the result of the cooling is the first halocarbon in solid form and the at least one second halocarbon in liquid or gaseous form.

7. The method of claim 6 further comprising the subsequent step of separating the liquid or gaseous second halocarbon from the solid first halocarbon.

8. The method of claim 7 wherein the separating is conducted by decantation, filtration, centrifuging, or outgassing under vacuum.

9. The method of claim 1 wherein the separating is conducted by decantation, filtration, centrifuging, or outgassing under vacuum.

10. The method of claim 1 wherein the cooling is conducted at a temperature of from about −150° C. to about 75° C.

11. The method of claim 1 wherein the cooling is conducted at a temperature of from about −130° C. to about 50° C.

12. The method of claim 1 wherein the cooling is conducted at a temperature of from about −120° C. to about 25° C.

13. The method of claim 1 wherein the first halocarbon is 2-chloro-1,1,1,2-tetrafluoropropane and the second halocarbon is 2-chloro-3,3,3-trifluoropropene.

14. The method of claim 1 wherein the 2-chloro-1,1,1,2-tetrafluoropropane and the 2-chloro-3,3,3-trifluoropropene form an azeotrope or azeotrope-like composition.

15. The method of claim 14 wherein the result of the cooling is solid 2-chloro-1,1,1,2-tetrafluoropropane and liquid or gaseous 2-chloro-3,3,3-trifluoropropene.

16. The method of claim 14 further comprising the subsequent step of separating 2-chloro-3,3,3-trifluoropropene from 2-chloro-1,1,1,2-tetrafluoropropane.

17. The method of claim 14 further comprising the subsequent step of separating liquid or gaseous 2-chloro-3,3,3-trifluoropropene from solid 2-chloro-1,1,1,2-tetrafluoropropane.

18. The method of claim 17 wherein the separating is conducted by decantation, filtration, centrifugation, degassation under vacuum.

19. The method of claim 14 wherein the cooling is conducted at a temperature of from about −85° C. to about −75° C.

20. The method of claim 14 wherein the cooling is conducted at a temperature of from about −81° C. to about −78° C.

* * * * *